United States Patent
Ni et al.

[11] Patent Number: 6,130,061
[45] Date of Patent: Oct. 10, 2000

[54] HUMAN STEM CELL ANTIGEN 2

[75] Inventors: Jian Ni, Rockville; Guo-Liang Yu, Darnestown; Reiner Gentz, Silver Spring; Jeannine D. Gocayne, Potomac, all of Md.

[73] Assignee: Human Genome Sciences, Inc., Rockville, Md.

[21] Appl. No.: 08/746,397

[22] Filed: Nov. 8, 1996

Related U.S. Application Data

[60] Provisional application No. 60/007,287, Nov. 9, 1995.

[51] Int. Cl.[7] .............................. C07H 21/00; C12N 1/15; C12N 1/21; C12N 5/10; C12N 15/12; C12N 15/63

[52] U.S. Cl. .................. 435/69.1; 435/320.1; 435/325; 435/252.3; 435/254.11; 536/23.1; 536/23.5

[58] Field of Search ................ 435/69.1, 320.1, 435/325, 252.3, 254.11; 536/23.1, 23.5

[56] References Cited

U.S. PATENT DOCUMENTS 5,468,612 11/1995 Cohen et al. .................................. 435/6

FOREIGN PATENT DOCUMENTS 9514772 1/1995 WIPO .

OTHER PUBLICATIONS

Genbank Accession No. H43804 (Oct. 15,1995).
Genbank Accession No. R50636 (Oct. 15, 1995).
Yamakawa et al. (1995) Human Molecular Genetics 4(4):709–716.
Boguski (1995) Trends Biochem. Sci. (TIBS) 20:295–296.
Saitoh et al. (1995) *J. Immunology* 155:5574–5581.
Spangrude et al. (1998) *J. Immunology* 141(11):3697–3707.
Classon et al. (1994) *PNAS* 91(12):5296–5300.
Classon et al. (1995) 9th International Congress of Immunology, p. 727, Abstr. No. 4312.
Antica et al. (1995) 9th International Congress of Immunology, p. 493, Abstr. No. 2923.

*Primary Examiner*—Scott D. Priebe
*Attorney, Agent, or Firm*—Human Genome Sciences, Inc.

[57] ABSTRACT

A human stem cell antigen 2 polypeptide and DNA (RNA) encoding such polypeptide and a procedure for producing such polypeptide by recombinant techniques is disclosed. Also disclosed are methods for utilizing such polypeptide for stimulating thymocyte maturation and differentiation, protecting neuronal cells, preventing rejection during organ transplantation, treating PNH, Alzheimer's Disease and inflammation is disclosed. Diagnostic assays for identifying mutations in nucleic acid sequence encoding a polypeptide of the present invention and for detecting altered levels of the polypeptide of the present invention for detecting diseases, for example, cancer, are also disclosed.

42 Claims, 3 Drawing Sheets

```
                    10                  30                  50
          GGACCGGGGGGCTCCGGGCCAGCCGCGGTCCAGAGCGCGCAAGGTTCGGGGAGCTCGGCC
                    70                  90                 110
          AGGCTGCTGGTACCTGCTTCCGCCCGGCGGACAGGCTGCTTTGGTTTGTAACCTCCAGGC
                   130                 150                 170
          AGGACGGCCATCCTCTCCAGAATGAAGATCTTCTTGCCAGTGCTGCTGGCTGCCCTTCTG
                             M   K   I   F   L   P   V   L   L   A   A   L   L
                   190                 210                 230
          GGTGTGGAGCGAGCCAGCTCGCTGATGTGCTTCTCCTGCTTGAACCAGAAGAGCAATCTG
           G   V   E   R   A   S   S   L   M   C   F   S   C   L   N   Q   K   S   N   L
                   250                 270                 290
          TACTGCCTGAAGCCGACCATCTGCTCCGACCAGGACAACTACTGCGTGACTGTGTCTGCT
           Y   C   L   K   P   T   I   C   S   D   Q   D   N   Y   C   V   T   V   S   A
                   310                 330                 350
          AGTGCCGGCATTGGGAATCTGGTGACATTTGGCCACAGCCTGAGCAAGACCTGTTCCCCG
           S   A   G   I   G   N   L   V   T   F   G   H   S   L   S   K   T   C   S   P
                   370                 390                 410
          GCCTGCCCCATCCCAGAAGGCGTCAATGTTGGTGTGGCTTCCATGGGCATCAGCTGCTGC
           A   C   P   I   P   E   G   V   N   V   G   V   A   S   M   G   I   S   C   C
                   430                 450                 470
          CAGAGCTTTCTGTGCAATTTCAGTGCGGGCGATGGCGGGCTGCGGGCAAGCGTCACCCTG
           Q   S   F   L   C   N   F   S   A   G   D   G   G   L   R   A   S   V   T   L
                   490                 510                 530
          CTGGGTGCCGGGCTGCTGCTGAGCCTGCTGCCGGCCCTGCTGCGGTTTGGCCCCTGACCG
           L   G   A   G   L   L   L   S   L   L   P   A   L   L   R   F   G   P   *
                   550                 570                 590
          CCCAGACCCTGTCCCCCGATCCCCCAGCTCAGGAAGGAAAGCCCAGCCCTTTCTGGATCC 610                 630                 650
          CACAGTGTATGGGAGCCCCTGACTCCTCACGTGCCTGATCTGTGCCCTTGGTCCCAGGTC 670                 690                 710
          AGGCCCACCCCCTGCACCTCCACCTGCCCCAGCCCCTGCCTCTGCCCCAAGTGGGGCCAG 730                 750                 770
          CTGCCCTCACTTCTGGGGTGGATGATGTGACCTTCCTTGGGGGACTGCGGAAGGGACGAG 790                 810                 830
          GGTTCCCTGGAGTCTTACGGTCCAACATCAGGACCAAGTCCCATGGACATGCTGACAGGG 850                 870                 890
          TCCCCAGGGAGACCGTGTCAGTAGGGATGTGTGCCTGGCTGTGTACGTGGGTGTGCAGTG
```

FIGURE 1  1/3

```
                910                     930                     950
CACGTGAGAGCACGTGGCGGCTTCTGGGGGCCATGTTTGGGGAGGGAGGTGTGCCAGCAG 970                     990                     1010
CCTGGAGAGCCTCAGTCCCTGTAGCCCCCTGCCCTGGCACAGCTGCATGCACTTCAAGGG 1030                    1050                    1070
 CAGCCTTTGGGGGTTGGGGTTTCTGCCACTTCCGGGTCTAGGCCCTGCCCCAAATCCAGC 1090                    1110                    1130
CAGTCCTGCCCCAGCCCACCCCCACATTGGAGCCCTCCTGCTGCTTTGGTGCCTCAAATA

1150
AATACAGATGTCCCCCAAAAAAA
```

FIGURE 1

```
  1 ......MKIFLPVLLAALLGVERASSLMCFSCLNQKSNLYCLKPTICSDQ 44
         |::||||||||||||:|.. |||||||| :||.|: ||.|. | :.
  1 MSATSNMRVFLPVLLAALLGMEQVHSLMCFSCTDQKNNINCLWPVSCQEK 50

45 DNYCVTVSASAGIGNLVTFGHSLSKTCSPACPIPE.GVNVGVASMGISCC 93
    |:||:|:||.||:|| |.:|..|.|.||| || .: .:|:||||:. ||
 51 DHYCITLSAAAGFGN.VNLGYTLNKGCSPICPSENVNLNLGVASVNSYCC 99

94 QSFLCNFSAGDGGLRASVTLLGAGLLLSLLPALLRFGP 131
    || :|||||:: ||||||:.||| |||||||| |||.::|
100 QSSFCNFSAAGLGLRASIPLLGLGLLLSLL.ALLQLSP 136
```

FIGURE 2

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 1163 BASE PAIRS
      (B) TYPE: NUCLEIC ACID
      (C) STRANDEDNESS: SINGLE
      (D) TOPOLOGY: LINEAR (ii) MOLECULE TYPE: cDNA (xi) SEQUENCE DESCRIPTION: SEQ ID NO:1:

```
GGACCGGGGG GCTCCGGGCC AGCCGCGGTC CAGAGCGCGC AAGGTTCGGG GAGCTCGGCC        60

AGGCTGCTGG TACCTGCTTC CGCCCGGCGG ACAGGCTGCT TTGGTTTGTA ACCTCCAGGC       120

AGGACGGCCA TCCTCTCCAG A ATG AAG ATC TTC TTG CCA GTG CTG CTG GCT        171
             Met Lys Ile Phe Leu Pro Val Leu Leu Ala
             -20                 -15

GCC CTT CTG GGT GTG GAG CGA GCC AGC TCG CTG ATG TGC TTC TCC TGC        219
Ala Leu Leu Gly Val Glu Arg Ala Ser Ser Leu Met Cys Phe Ser Cys
-10                 -5                   1                   5

TTG AAC CAG AAG AGC AAT CTG TAC TGC CTG AAG CCG ACC ATC TGC TCC        267
Leu Asn Gln Lys Ser Asn Leu Tyr Cys Leu Lys Pro Thr Ile Cys Ser
 10                  15                  20

GAC CAG GAC AAC TAC TGC GTG ACT GTG TCT GCT AGT GCC GGC ATT GGG        315
Asp Gln Asp Asn Tyr Cys Val Thr Val Ser Ala Ser Ala Gly Ile Gly
 25                  30                  35

AAT CTG GTG ACA TTT GGC CAC AGC CTG AGC AAG ACC TGT TCC CCG GCC        363
Asn Leu Val Thr Phe Gly His Ser Leu Ser Lys Thr Cys Ser Pro Ala
 40                  45                  50

TGC CCC ATC CCA GAA GGC GTC AAT GTT GGT GTG GCT TCC ATG GGC ATC        411
Cys Pro Ile Pro Glu Gly Val Asn Val Gly Val Ala Ser Met Gly Ile
 55                  60                  65                  70

AGC TGC TGC CAG AGC TTT CTG TGC AAT TTC AGT GCG GGC GAT GGC GGG        459
Ser Cys Cys Gln Ser Phe Leu Cys Asn Phe Ser Ala Gly Asp Gly Gly
 75                  80                  85

CTG CGG GCA AGC GTC ACC CTG CTG GGT GCC GGG CTG CTG CTG AGC CTG        507
Leu Arg Ala Ser Val Thr Leu Leu Gly Ala Gly Leu Leu Leu Ser Leu
 90                  95                  100

CTG CCG GCC CTG CTG CGG TTT GGC CCC TGA CCGCCCAGAC CCTGTCCCCC          557
Leu Pro Ala Leu Leu Arg Phe Gly Pro
105                 110

GATCCCCCAG CTCAGGAAGG AAAGCCCAGC CCTTTCTGGA TCCCACAGTG TATGGGAGCC      617

CCTGACTCCT CACGTGCCTG ATCTGTGCCC TTGGTCCCAG GTCAGGCCCA CCCCCTGCAC      677

CTCCACCTGC CCCAGCCCCT GCCTCTGCCC CAAGTGGGGC CAGCTGCCCT CACTTCTGGG      737

GTGGATGATG TGACCTTCCT TGGGGGACTG CGGAAGGGAC GAGGGTTCCC TGGAGTCTTA      797

CGGTCCAACA TCAGGACCAA GTCCCATGGA CATGCTGACA GGGTCCCCAG GGAGACCGTG      857
```

```
TCAGTAGGGA TGTGTGCCTG GCTGTGTACG TGGGTGTGCA GTGCACGTGA GAGCACGTGG      917

CGGCTTCTGG GGGCCATGTT TGGGGAGGGA GGTGTGCCAG CAGCCTGGAG AGCCTCAGTC      977

CCTGTAGCCC CCTGCCCTGG CACAGCTGCA TGCACTTCAA GGGCAGCCTT TGGGGGTTGG    1037

GGTTTCTGCC ACTTCCGGGT CTAGGCCCTG CCCCAAATCC AGCCAGTCCT GCCCCAGCCC    1097

ACCCCCACAT TGGAGCCCTC CTGCTGCTTT GGTGCCTCAA ATAAATACAG ATGTCCCCCA    1157

AAAAAA                                                                1163
```

(2) INFORMATION FOR SEQ ID NO:2:

(i) SEQUENCE CHARACTERISTICS:
        (A) LENGTH: 131 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:2:

```
Met Lys Ile Phe Leu Pro Val Leu Leu Ala Ala Leu Leu Gly Val
-20              -15                  -10

Glu Arg Ala Ser Ser Leu Met Cys Phe Ser Cys Leu Asn Gln Lys
 -5                   1               5                  10

Ser Asn Leu Tyr Cys Leu Lys Pro Thr Ile Cys Ser Asp Gln Asp
                15              20                      25

Asn Tyr Cys Val Thr Val Ser Ala Ser Ala Gly Ile Gly Asn Leu
             25              30              35

Val Thr Phe Gly His Ser Leu Ser Lys Thr Cys Ser Pro Ala Cys
             40              45              50

Pro Ile Pro Glu Gly Val Asn Val Gly Val Ala Ser Met Gly Ile
             55              60              65

Ser Cys Cys Gln Ser Phe Leu Cys Asn Phe Ser Ala Gly Asp Gly
             70              75              80

Gly Leu Arg Ala Ser Val Thr Leu Leu Gly Ala Gly Leu Leu Leu
             85              90              100

Ser Leu Leu Pro Ala Leu Leu Arg Phe Gly Pro
            105             110
```

(2) INFORMATION FOR SEQ ID NO:3:

(i) SEQUENCE CHARACTERISTICS:
        (A) LENGTH: 23 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:3:

```
CGCGGATCCA TGCTGATGTG CTT                                               23
```

(2) INFORMATION FOR SEQ ID NO:4:

(i) SEQUENCE CHARACTERISTICS:
        (A) LENGTH: 28 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:4:

CGCGGATCCC TACGCACTGA AATTGCAC                                    28

(2) INFORMATION FOR SEQ ID NO:5:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:5:

CGCGGATCCG CCATCATGAA GATCTTCTTG                                  30

(2) INFORMATION FOR SEQ ID NO:6:

(i) SEQUENCE CHARACTERISTICS:
        (A) LENGTH: 28 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:6:

CGCGGATCCC TACGCACTGA AATTGCAC                                    28

(2) INFORMATION FOR SEQ ID NO:7:

(i) SEQUENCE CHARACTERISTICS:
        (A) LENGTH: 21 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:7:

CGCGGATCCC CTGATGTGCT T                                           21

(2) INFORMATION FOR SEQ ID NO:8:

(i) SEQUENCE CHARACTERISTICS:
        (A) LENGTH: 27 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:8:

CGCGGATCCC TACAACCCGC CATCGCC                                     27

(2) INFORMATION FOR SEQ ID NO:9:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:9:

CGCGGATCCG CCATCATGAA GATCTTCTTG                                  30

(2) INFORMATION FOR SEQ ID NO:10:

(i) SEQUENCE CHARACTERISTICS:
        (A) LENGTH: 71 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:10:

```
GCGCTCTAGA TCAAGCGTAG TCTGGGACGT CGTATGGGTA CAACCCGCCA TCGCCCGCAC      60

TGAAATTGCA C                                                          71
```

(2) INFORMATION FOR SEQ ID NO:11:

(i) SEQUENCE CHARACTERISTICS:
        (A) LENGTH: 138 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:11:

```
Met Ser Ala Thr Ser Asn Met Arg Val Phe Leu Pro Val Leu Leu
                 5                  10                  15

Ala Ala Leu Leu Gly Met Glu Gln Val His Ser Leu Met Cys Phe
                20                  25                  30

Ser Cys Thr Asp Gln Lys Asn Asn Ile Asn Cys Leu Trp Pro Val
                35                  40                  45

Ser Cys Gln Glu Lys Asp His Tyr Cys Ile Thr Leu Ser Ala Ala
                50                  55                  60

Ala Gly Phe Gly Asn Xaa Val Asn Leu Gly Tyr Thr Leu Asn Lys
                65                  70                  75

Gly Cys Ser Pro Ile Cys Pro Ser Glu Asn Val Asn Leu Asn Leu
                80                  85                  90

Gly Val Ala Ser Val Asn Ser Tyr Cys Cys Gln Ser Ser Phe Cys
                95                 100                 105

Asn Phe Ser Ala Ala Gly Leu Gly Leu Arg Ala Ser Ile Pro Leu
               110                 115                 120

Leu Gly Leu Gly Leu Leu Leu Ser Leu Leu Xaa Ala Leu Leu Gln
               125                 130                 135

Leu Ser Pro
```

HUMAN STEM CELL ANTIGEN 2

This application is entitled to the benefits of 35 U.S.C. § 119(e) based on U.S. Provisional Application 60/007,287, filed Nov. 9, 1995, pending.

This invention relates to newly identified polynucleotides, polypeptides encoded by such polynucleotides, the use of such polynucleotides and polypeptides, as well as the production of such polynucleotides and polypeptides. More particularly, the polypeptide of the present invention has been putatively identified as human stem cell antigen 2, sometimes hereinafter referred to as "hSca-2". The invention also relates to inhibiting the action of such polypeptides.

The Ly-6 family of cell surface proteins is a group of molecules differentially expressed in several hematopoietic lineages that appears to function in signal transduction and cell activation. Ly-6 antigens are encoded by a multi-gene family and are expressed in both lymphoid and non-lymphoid cells. The Ly-6 super family of molecules includes human CD59, a cell surface protein which protects human complement-mediated membrane damage, squid Sgp1 and Sgp2, urokinase plasminogen activator receptor and murine Sca-1 and Sca-2.

In all of these molecules with the exception of the squid Sgp1 and 2, there are 10 cysteine residues which have a conserved motif and a glycosyl phosphatidylinositol (GPI) anchor at the COOH-terminus. Further, there are clear areas of identity between the members at the amino acid level. Moreover, there are normally 3 to 5 amino acids between cysteines 6 and 7 and the cysteine 8 and cysteine 9 residues are adjacent. An alanine residue is found one residue upstream of the GPI anchor. The GPI anchor is necessary to anchor these cell surface proteins into the lipid bilayer membrane on the outside of the cell surface.

The cell surface phenotype of the intrathymic precursors is similar to that of bone marrow stem cells, except that the former express murine Sca-2 (Wu, L. et al, J. Exp. Med., 174:1617–1627 (1991)). Murine Sca-2 is also expressed by the majority of immature thymocytes, but not by mature peripheral T-cells. Murine Sca-2 is also expressed on B22+ bone marrow cells and peripheral B-cells (Spangrude, G. J. et al., J. Immunol., 141:3697–3707 (1988)). The mature murine Sca-2 protein contains 82 amino acids with a predicted molecular mass of 8.8 kDa. This sequence contains a relatively high proportion of cysteine residues (10/82), which suggests that numerous disulfide bonds stabilize this tertiary structure of murine Sca-2. There is one consensus sequence for N-linked oligosaccharide attachment (Asn-79). Ser-51 and Ser-56 are both flanked by Pro residues and may be O-glycosylated (Jentoft, N., Trends Biochem. Sci., 15:291–294 (1990)) and (Gooley, A A et al., Biochem. Biophys. Res. Commun., 178:1194–1201 (1991)).

Murine Sca-2 shows significant structural similarities to mouse Ly-6 antigens, human CD59 and a herpes virus CD59 homolog. A remarkable conservation of all extracellular cysteine residues is evident, with all ten cysteine residues in the putative mature protein conserved between Murine Sca-2 and other sequences. There is clearly an evolutionary relationship between Murine Sca-2 and the Ly-6 family.

The C-terminus of the Sca-2 protein is enriched for hydrophobic amino acids, indicating that it is probably a signal peptide for the attachment of a GPI moiety for cell membrane anchoring (Ferguson, M. A. and Williams, A. F., Annu. Rev. Biochem., 57:285–320 (1988)). All sequences of the Ly-6 family have C-terminal hydrophobic signal sequences of GPI attachment or have a GPI anchor. The GPI signal sequence directs attachment of a GPI anchor to the c-terminus of murine Sca-2 and this modification occurs in both thymocytes and COS cells. The conservation of the Cys-Asn sequence near the C-terminus of the mature protein in all members of the Ly-6 family suggest a consensus attachment point for the GPI anchor since the corresponding Asn residue in Sgp-2 has been empirically determined as the C-terminal amino acid (Williams, A F et al., Immunogenetics, 27:265–272 (1988)). Data for known GPI attachment sites suggests that Ala-82 is the C-terminal amino acid of murine Sca-2 (Ferguson, M A and Williams, A. F., Annu. Rev. Biochem., 57:285–320 (1988)).

GPI-linked molecules have been implicated in signal transduction in hematopoietic cells, suggesting an important role for the GPI anchor and cell activation. (Robinson, P J, Immunol. Today, 12:35–41 (1991)). It is possible that Sca-2 may also function as a signal transduction molecule, and the presence of a GPI anchor suggests a signalling mechanism in common with other GPI-anchored molecules.

This cytolytic activity of human complement is mediated by the assembly of five proteins (c5b, c6, c7, c8 and c9) into a functional membrane attack complex. The c5b-9 complex forms stable pores in the membrane, thereby altering the ion permeability of the cell. This can lead to cell lysis or, in some case, sub-lytic activation. The hemolytic anemia associated with paroxysmal nocturnal hemoglobinuria (PNH) can be attributed to increased csb-9 deposition on erythrocytes. Thrombosis seen in PNH patients may be caused by increased c5b-9 deposition on platelets, which leads to pro-coagulation responses such as increased prothrombinase activity. Normally, human blood cells are protected against autologous complement activation by membrane proteins that block the assembly of functional complement pores. One such protein is human CD59 which inhibits the assembly of c5b-9 by interacting with c8 and c9. Accordingly, administration of CD59 prevents hemolytic disease or thrombosis.

Further, the CD59 protein may prevent the complement mediated lysis and activation of endothelial cells which leads to hyper acute rejection and therefore may be administered during xenogeneic organ transplantation. Further, a protein extracted from a urate-calcium oxalate stone has shown high homology to the CD59 protein. (Binette, J. P. and Binette, M. B., Scanning Microcs., 7:1107–10 (1993)).

CD59 is also thought to retard the onset of Alzheimer's disease since a detection of the membrane inhibitor of reactive lysis (CD59) has been found in the diseased neurons of the Alzheimer brain, (McGeer, P. L. et al., Brain Research, 544:315–9 (1991)).

Urokinase plasminogen activator receptor is also a member of this family and binds plasminogen activator and thus presumably concentrates this protease at a cell surface where it is required and, therefore, may also be considered to act within this functional framework. It is thought that plasminogen activator may be involved in the penetration of extracellular matrices and that its function may be important in metastasis as well as in non-pathogenic functions. (Roldin, et al., EMBO J., 9:467–474 (1990)).

The polypeptide of the present invention has been putatively identified as a human Sca-2 protein as a result of amino acid sequence homology to murine Sca-2, and, therefore, as a member of the Ly-6 protein super-family.

In accordance with one aspect of the present invention, there is provided a novel mature polypeptide, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention including mRNAs, cDNAs, genomic DNAs as well as analogs and biologically active and diagnostically or therapeutically useful fragments thereof.

In accordance with another aspect of the present invention there is provided an isolated nucleic acid molecule encoding a mature polypeptide expressed by the DNA contained in ATCC Deposit No. 97301.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptide, or polynucleotide encoding such polypeptide for therapeutic purposes, for example, to stimulate the maturation and differentiation of the thymocytes, to prevent damage from the complement c5b-9, to prevent hyper-acute rejection, to treat PNH and to treat Alzheimer's disease.

In accordance with yet a further aspect of the present invention, there are provided antibodies against such polypeptides.

In accordance with another aspect of the present invention, there are provided hSca-2 agonists which mimic hSca-2.

In accordance with yet another aspect of the present invention, there are provided antagonists to such polypeptides, which may be used to inhibit the action of such polypeptides, for example, in the treatment of neoplasia by preventing tumor metastasis.

In accordance with yet a further aspect of the present invention, there is also provided nucleic acid probes comprising nucleic acid molecules of sufficient length to specifically hybridize to a nucleic acid sequence of the present invention.

In accordance with still another aspect of the present invention, there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 is an illustration of the cDNA (SEQ ID NO.1) and corresponding deduced amino acid sequence (SEQ ID NO:2) of the polypeptide of the present invention. The initial 20 amino acids (underlined) represent a leader sequence and the terminal 29 amino acids (double underlined) represent the GPI anchor. Sequencing was performed using a 373 automated DNA sequencer (Applied Biosystems, Inc.).

FIG. 2 is an amino acid sequence comparison between the polypeptide of the present invention (top line) and the murine Sca-2 precursor (SEQ ID NO:11)

In accordance with an aspect of the present invention, there is provided an isolated nucleic acid (polynucleotide) which encodes for the mature polypeptide having the deduced amino acid sequence of FIG. 1 (SEQ ID NO:2).

A polynucleotide encoding a polypeptide of the present invention may be obtained from activated T-cells, human thymus and human cerebellum. The polynucleotide of this invention was discovered in a cDNA library derived from human cerebellum. It is structurally related to the Ly-6 super-family. It contains an open reading frame encoding a protein of 131 amino acid residues. The first 20 amino acids residues represent a putative leader sequence and the terminal 29 amino acids represent a GPI anchor. Accordingly, the protein may exist as a soluble extracellular protein comprising 81 amino acids after the protein is cleaved from the GPI anchor and the putative leader portion has been removed. The protein exhibits the highest degree of homology at the nucleotide level to murine hSca-2 precursor mRNA with 68% identity and 68% similarity over a 185 base pair stretch. The protein also exhibits the highest degree of homology at the amino acid level to murine Sca-2 precursor with 61.240% identity and 77.519% similarity over the entire amino acid stretch. The molecular weight is 13494.70; the molar extinction coefficient is 3760 and the isoelectric point is 7.79.

The polypeptide of the present invention contains conserved motifs characteristic of members of the Ly-6 super-family. The conserved cysteine residues are conserved in the polypeptide of the present invention, namely, 10 cysteines are shown and are located in similar positions to other members of the family. For example, there are three amino acids between cysteine 6 and cysteine 7 and cysteine 8 and cysteine 9 are adjacent. Further, the GPI anchor comprises a stretch hydrophobic amino acids which is present in the polypeptide of the present invention and a terminal alanine residue on the mature protein is present directly prior to the GPI anchor.

In accordance with another aspect of the present invention there are provided isolated polynucleotides encoding a mature polypeptide expressed by the DNA contained in ATCC Deposit No. 97301, deposited with the American Type Culture Collection, 10801 University Boulevard, Manassas, Va. 20110-2209, USA, on Sep. 25, 1995. The deposited material is a cDNA encoding the full-length hSca-2 polypeptide inserted into a pBluescript SK(-) vector (Stratagene, La Jolla, Calif.).

The deposit(s) has been made under the terms of the Budapest Treaty on the International Recognition of the Deposit of Micro-organisms for purposes of Patent Procedure. The strain will be irrevocably and without restriction or condition released to the public upon the issuance of a patent. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are controlling in the event of any conflict with any description of sequences herein. A license may be required to make, use or sell the deposited materials, and no such license is hereby granted.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or may be a different coding sequence, which coding sequence, as a result of the redundancy or degeneracy of the genetic code, encodes the same mature polypeptide as the DNA of FIG. 1 (SEQ ID NO:1).

The polynucleotide which encodes for the mature polypeptide of FIG. 1 (SEQ ID NO:2) may include, but is not limited to: only the coding sequence for the mature polypeptide; the coding sequence for the mature polypeptide and additional coding sequence such as a leader or secretory sequence, a proprotein sequence and a membrane anchor; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide" as used for the present invention encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2). Variants of the polynucleotide may be naturally occurring allelic variants of the polynucleotide or a non-naturally occurring variant of the polynucleotide.

Thus, the present invention includes polynucleotides encoding the same mature polypeptide as shown in FIG. 1 (SEQ ID NO:2) as well as variants of such polynucleotides, which variants encode for a fragment, derivative or analog of the polypeptide of FIG. 1 (SEQ ID NO:2). Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1). As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell and a transmembrane anchor which facilitates attachment of the polypeptide to a cellular membrane. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, for a protein having a prosequence, for a protein having a transmembrane anchor or for a polypeptide having a prosequence, a presequence (leader sequence) and a transmembrane anchor.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length polynucleotide of the present invention may be used as a hybridization probe for a cDNA library to isolate the full length cDNA and to isolate other cDNAs which have a high sequence similarity to the gene or similar biological activity. Probes of this type preferably have at least 15 bases, may have at least 30 bases and may also contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 75%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNA of FIG. 1 (SEQ ID NO:1).

Alternatively, the polynucleotide may have at least 15 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 75% identity, preferably at least 90% and more preferably at least a 95% identity to a polynucleotide which encodes the polypeptide of SEQ ID NO:2 and polynucleotides complementary thereto as well as portions thereof, which portions have at least 30 consecutive bases and preferably at least 50 consecutive bases and to polypeptides encoded by such polynucleotides.

The present invention further relates to a polypeptide which has the deduced amino acid sequence of FIG. 1 (SEQ ID NO:2), as well as fragments, analogs and derivatives of such polypeptide.

The terms "fragment," "derivative" and "analog" when referring to the polypeptide of FIG. 1 (SEQ ID NO:2), means a polypeptide which retains essentially the same biological function or activity as such polypeptide. Thus, an analog includes a proprotein which can be activated by cleavage of the proprotein portion to produce an active mature polypeptide. Such fragments, derivatives and analogs must have sufficient similarity to the polypeptide of SEQ ID NO:2 so that activity of the native polypeptide is retained.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% identity to the polypeptide of SEQ ID NO:2, or which have, at least 90% similarity (at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli,* Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae Trp1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotide and polypeptide of the present invention may be employed to stimulate thymocyte maturation and differentiation.

The polypeptide of the present invention may also be employed to protect astrocytes during inflammatory and infectious disorders of the nervous system.

The polypeptide of the present invention may also be employed to prevent complement-mediated lysis and activation of endothelial cells for the treatment of hyper-acute rejection. In this manner, the polypeptide of the present invention may be employed during xenogeneic organ transplantation.

The polypeptide of the present invention may also be employed to prevent and/or treat PNH and the associated disorders, for example, hemolytic anemia, pancytopenia and venous thrombosis. Retroviral gene therapy with the hSca-2 polynucleotide could also provide a treatment for PNH patients.

The polypeptide of the present invention may also provide a treatment for Alzheimer's disease which is characterized by lysis of neuronal cells.

The polypeptide of the present invention may also be employed as an anti-inflammatory, anti-coagulant and as an anti-tumoral agent.

The polypeptide of the present invention may also be involved in antigen presentation to obtain an immune response. Thus, the polypeptide according to the invention may be employed to study the immune response in a host as it relates to antigen presentation.

The polynucleotides and polypeptides of the present invention may be employed as research reagents and materials for discovery of treatments and diagnostics to human disease.

This invention provides a method for identification of the receptor for hSca-2. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to hSca-2, and a cDNA library created from this RNA is divided into pools and used to transfect COS cells or other cells that are not responsive to hSca-2. Transfected cells which are grown on glass slides are exposed to labeled hSca-2. hSca-2 can be labeled by a variety of means including iodination or inclusion of a recognition site for a site-specific protein kinase. Following fixation and incubation, the slides are subjected to auto-radiographic analysis. Positive pools are identified and sub-pools are prepared and re-transfected using an iterative sub-pooling and rescreening process, eventually yielding a single clone that encodes the putative receptor. As an alternative approach for receptor identification, labeled ligand can be photoaffinity linked with cell membrane or extract preparations that express the receptor molecule. Cross-linked material is resolved by PAGE and exposed to X-ray film. The labeled complex containing the ligand-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention provides a method of screening compounds to identify those which enhance (agonists) or block (antagonists) interaction of hSca-2 with its receptor. As an example, a mammalian cell or membrane preparation expressing the hSca-2 receptor would be incubated with labeled hSca-2 in the presence of the compound. The ability of the compound to enhance or block this interaction could then be measured. Alternatively, the response of a known second messenger system following interaction of hSca-2 and receptor would be measured and compared in the presence or absence of the compounds. Such second messenger systems include but are not limited to, cAMP guanylate cyclase, ion channels or phosphoinositide hydrolysis.

The present invention also relates to an assay for identifying potential antagonists specific to hSca-2. An example of such an assay combines hSca-2 and a potential antagonist with membrane-bound hSca-2 receptors or recombinant hSca-2 receptors under appropriate conditions for a competitive inhibition assay. hSca-2 can be labeled, such as by radioactivity, such that the number of hSca-2 molecules bound to the receptor will determine the effectiveness of the potential antagonist.

Potential antagonists include an antibody, or in some cases, an oligopeptide, which binds to the polypeptide. Alternatively, a potential antagonist may be a closely related protein which binds to the receptor sites, however, they are inactive forms of the polypeptide and thereby prevent the action of hSca-2 since receptor sites are occupied.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of hSca-2. The antisense RNA oligonucleotide hybridizes to the mRNA in vivo and blocks translation of the mRNA molecule into hSca-2 polypeptide (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of hSca-2.

Potential antagonists include a small molecule which binds to and occupies the catalytic site of the polypeptide thereby making the catalytic site inaccessible to substrate such that normal biological activity is prevented. Examples of small molecules include but are not limited to small peptides or peptide-like molecules.

The antagonists may be employed to prevent tumor metastasis of cancer cells and therefore to prevent or treat neoplasia. The antagonists may be employed in a composition with a pharmaceutically acceptable carrier, e.g., as hereinafter described.

The polypeptides of the present invention or antagonists may be employed in combination with a suitable pharmaceutical carrier. Such compositions comprise a therapeutically effective amount of the polypeptide or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the oral, topical, parenterally, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The hSca-2 polypeptides and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechnicues*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19–14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene will allow a diagnosis of a disease or a susceptibility to a disease which results from expression of a mutated hSca-2 polypeptide.

Individuals carrying mutations in the gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding hSca-2 can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptide of the present invention in various tissues since an over-expression of the proteins compared to normal control tissue samples can detect the presence of neoplasia. Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to the hSca-2 antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any of the polypeptide of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the polypeptide of the present invention present in a given volume of patient sample a when compared against a standard curve.

A competition assay may be employed wherein antibodies specific to the polypeptide of the present invention are attached to a solid support and labeled hSca-2 and a sample derived from the host are passed over the solid support and the amount of label detected attached to the solid support can be correlated to a quantity of the polypeptide of the present invention in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 $\mu$g of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of Soluble Extracellular hSca-2

The DNA sequence encoding hSca-2, ATCC # 97301, is initially amplified using PCR oligonucleotide primers corresponding to the 5' sequences of the processed hSca-2 protein (minus the signal peptide sequence) and the vector sequences 3' to the hSca-2 gene. Additional nucleotides corresponding to Sca-2 were added to the 5' and 3' sequences respectively. The 5' oligonucleotide primer has the sequence 5° CGCGGATCCATGCTGATGTGCTT 3' (SEQ ID NO:3) contains a BamHI restriction enzyme site followed by 14 nucleotides of hSca-2 coding sequence starting from the presumed terminal amino acid of the processed protein codon. The 3' sequence 5' CGCGGATCCCTACGCACT-GAAATTGCAC 3' (SEQ ID NO:4) contains complementary sequences to BamHI site and is followed by 18 nucleotides of hSca-2. The restriction enzyme sites correspond to the restriction enzyme sites on the bacterial expression vector pQE-60. (Qiagen, Inc., Chatsworth, Calif., 91311). pQE-60 encodes antibiotic resistance (Amp'), a bacterial origin of replication (ori), an IPTG-regulatable promoter operator (P/O), a ribosome binding site (RBS), a 6-His tag and restriction enzyme sites. pQE-60 was then digested with BamhI. The amplified sequences were ligated into pQE-60 and were inserted in frame with the sequence encoding for the histidine tag and the RBS. The ligation mixture was then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized hSca-2 was purified from this solution by chromatography on a Nickel-Chelate column under conditions that allow for tight binding by proteins containing the 6-His tag (Hochuli, E. et al., J. Chromatography 411:177–184 (1984)). hSca-2 (95% pure was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2

Cloning and Expression of Soluble Extracellular hSca-2 using the Baculovirus Expression System The DNA sequence encoding the full length hSca-2 protein, ATCC # 97301, was amplified using PCR oligonucleotide primers corresponding to the 5' and 3' sequences of the gene:

The 5' primer has the sequence 5° CGCGGATCCGCCA TCATGAAGATCTTCTTG 3' (SEQ ID NO:5) and contains a BamHI restriction enzyme site (in bold) followed by 6 nucleotides resembling an efficient signal for the initiation of translation in eukaryotic cells (Kozak, M., J. Mol. Biol., 196:947–950 (1987) which is just behind the first 15 nucleotides of the hSca-2 gene (the initiation codon for translation "ATG" is underlined).

The 3' primer has the sequence 5° CGCGGATCCCTA CGCACTGAAATTGCAC 3' (SEQ ID NO:6) and contains the cleavage site for the restriction endonuclease BamHI and 18 nucleotides complementary to the 3' translated sequence of the extracellular part of hSca-2. The amplified sequences were isolated from a 1% agarose gel using a commercially available kit ("Geneclean, " BIO 101 Inc., La Jolla, Calif.). The fragment was then digested with the endonucleases BamHI, and purified again on a 1% agarose gel. This fragment is designated F2.

The vector pA2 (modification of pVL941 vector, discussed below) is used for the expression of the hSca-2 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI. The polyadenylation site of the simian virus (SV)40 is used for efficient polyadenylation. For an easy selection of recombinant virus the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pA2 such as pRG1 and pA2-GP in which case the 5' primer is 5° CGCGGATC-CCCTGATGTGCTT 3' (SEQ ID NO:7) and the 3' primer is 5° CGCGGATCCCTACAACCCG CCATCGCC 3' (SEQ ID NO:8), pAc373, pVL941 and pAcIM1 (Luckow, V. A. and Summers, M. D., Virology, 170:31–39).

The plasmid was digested with the restriction enzyme BamHI and then dephosphorylated using calf intestinal phosphatase by procedures known in the art. The DNA was then isolated from a 1% agarose gel using the commercially available kit ("Geneclean " BIO 101 Inc., La Jolla, Calif.). This vector DNA is designated V2.

Fragment F2 and the dephosphorylated plasmid V2 were ligated with T4 DNA ligase. E.coli HB101 cells were then transformed and bacteria identified that contained the plasmid (pBachSca-2) with the hSca-2 gene using the enzyme BamHI. The sequence of the cloned fragment was confirmed by DNA sequencing.

5 µg of the plasmid pBachSca-2 was co-transfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBachSca-2 were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added drop-wise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal " (Life Technologies Inc., Gaithersburg) was used which allows an easy isolation of blue stained plaques. (A detailed description of a "plaque assay " can also be found in the user's guide for insect cell culture and baculovirology distributed by Life Technologies Inc., Gaithersburg, page 9–10).

Four days after the serial dilution, the virus was added to the cells and blue stained plaques were picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-hSca-2 at a multiplicity of infection (MOI) of 2. Six hours later the medium was removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) were added. The cells were further incubated for 16 hours before they were harvested by centrifugation and the labelled proteins visualized by SDS-PAGE and autoradiography.

EXAMPLE 3

Expression of Recombinant hSca-2 in COS Cells

The expression of plasmid, hSca-2 HA is derived from a vector pcDNAI/Amp (Invitrogen) containing: 1) SV40 origin of replication, 2) ampicillin resistance gene, 3) E.coli replication origin, 4) CMV promoter followed by a polylinker region, an SV40 intron and polyadenylation site. A DNA fragment encoding the entire hSca-2 precursor and a HA tag fused in frame to its 3' end was cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The plasmid construction strategy is described as follows:

The DNA sequence encoding hSca-2, ATCC # 97301, was constructed by PCR using two primers: the 5' primer 5' CGCGGATCCGCCATCATGAAGATCTTCTTG 3' (SEQ ID NO:9) contains a BamHI site followed by hSca-2 coding sequence starting from the initiation codon; the 3' sequence 5' GCGCTCTAGATCAA GCGTAGTCTGGGACGTCG-TATGGGTACAACCCGCCATCGCCCG-CACTGAAATTGCAC3' (SEQ ID NO:10) contains complementary sequences to XbaI site, translation stop codon, HA tag and hSca-2 coding sequence (not including the stop codon). Therefore, the PCR product contains a BamHI site, hSca-2 coding sequence followed by HA tag fused in frame, a translation termination stop codon next to the HA tag, and an XbaI site. The PCR amplified DNA fragment and the vector, pcDNAI/Amp, were digested with BamHI and XbaI restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant hSca-2 COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the hSca-2 HA protein was detected by radiolabelling and immunoprecipation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media was then collected and cells were lysed with detergent (RIPA buffer (150 mM NaCl, 1% NP-40, 0.1 SDS, 1% NP-40, 0.5% DOC, 50 mM Tris, pH 7.5) (Wilson, I. et al., Id. 37:767 (1984)). Both cell lysate and culture media were precipitated with an HA specific monoclonal antibody. Proteins precipitated were analyzed on 15% SDS-PAGE gels.

EXAMPLE 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a nucleic acid sequence selected from the group consisting of:
    (a) a polynucleotide encoding amino acids −20 to 111 of SEQ ID NO:2;
    (b) a polynucleotide encoding amino acids 1 to 111 of SEQ ID NO:2;
    (c) a polynucleotide encoding the amino acid sequence encoded by the cDNA contained in ATCC Deposit No. 97301
    (d) a polynucleotide encoding the amino acid sequence encoded by the cDNA contained in ATCC Deposit No. 97301, wherein the amino acid sequence lacks a signal sequence; and
    (e) the complement of (a), (b), (c), or (d).

2. The isolated polynucleotide of claim 1, wherein said polynucleotide is (a).

3. The isolated polynucleotide of claim 2, which comprises nucleotides 142 to 534 of SEQ ID NO:1.

4. The isolated polynucleotide of claim 1, wherein said polynucleotide is (b).

5. The isolated polynucleotide of claim 4, which comprises nucleotides 202 to 534 of SEQ ID NO:1.

6. The isolated polynucleotide of claim 1, wherein said polynucleotide is (c).

7. The isolated polynucleotide of claim 1, wherein said polynucleotide is (d).

8. The isolated polynucleotide of claim 1, wherein said polynucleotide is (e).

9. The isolated polynucleotide of claim 1, wherein the polynucleotide is double stranded.

10. An isolated polynucleotide consisting of a nucleic acid sequence selected from the group consisting of:

(a) a polynucleotide encoding amino acids −20 to 111 of SEQ ID NO:2;

(b) a polynucleotide encoding amino acids 1 to 111 of SEQ ID NO:2;

(c) a polynucleotide encoding the amino acid sequence encoded by the cDNA contained in ATCC Deposit No. 97301

(d) a polynucleotide encoding the amino acid sequence encoded by the cDNA contained in ATCC Deposit No. 97301, wherein the amino acid sequence lacks a signal sequence; and (e) the complement of (a), (b), (c), or (d).

11. The isolated polynucleotide of claim 10, wherein said polynucleotide is (a).

12. The isolated polynucleotide of claim 11, which comprises nucleotides 142 to 534 of SEQ ID NO:1.

13. The isolated polynucleotide of claim 10, wherein said polynucleotide is (b).

14. The isolated polynucleotide of claim 13, which comprises nucleotides 102 to 534 of SEQ ID NO:1.

15. The isolated polynucleotide of claim 10, wherein said polynucleotide is (c).

16. The isolated polynucleotide of claim 10, wherein said polynucleotide is (d).

17. The isolated polynucleotide of claim 10, wherein said polynucleotide is (e).

18. The isolated polynucleotide of claim 10, wherein the polynucleotide is double stranded.

19. The isolated polynucleotide of claim 2, further comprising a heterologous polynucleotide.

20. The isolated polynucleotide of claim 19, wherein the heterologous polynucleotide encodes a heterologous polypeptide.

21. A vector comprising the polynucleotide of claim 2.

22. An isolated host cell comprising the polynucleotide of claim 2, wherein said polynucleotide is operatively associated with a heterologous regulatory sequence.

23. A method of producing a polypeptide comprising:

(a) culturing the host cell of claim 22 under conditions such that said polypeptide is expressed; and (b) recovering said polypeptide.

24. The isolated polynucleotide of claim 4, further comprising a heterologous polynucleotide.

25. The isolated polynucleotide of claim 24, wherein the heterologous polynucleotide encodes a heterologous polypeptide.

26. A vector comprising the polynucleotide of claim 4.

27. An isolated host cell comprising the polynucleotide of claim 4, wherein said polynucleotide is operatively associated with a heterologous regulatory sequence.

28. A method of producing apolypeptide comprising:

(a) culturing the host cell of claim 27 under conditions such that said polypeptide is expressed; and (b) recovering said polypeptide.

29. The isolated polynucleotide of claim 6, further comprising a heterologous polynucleotide.

30. The isolated polynucleotide of 29, wherein the heterologous polynucleotide encodes a heterologous polypeptide.

31. A vector comprising the polynucleotide of claim 6.

32. An isolated host cell comprising the polynucleotide of claim 6, wherein said polynucleotide is operatively associated with a heterologous regulatory sequence.

33. A method of producing a polypeptide comprising:

(a) culturing the host cell of claim 32 under conditions such that said polypeptide is expressed; and (b) recovering said polypeptide.

34. The isolated polynucleotide of claim 7, further comprising a heterologous polynucleotide.

35. The isolated polynucleotide of 34, wherein the heterologous polynucleotide encodes a heterologous polypeptide.

36. A vector comprising the polynucleotide of claim 7.

37. An isolated host cell comprising the polynucleotide of claim 7, wherein said polynucleotide is operatively associated with a heterologous regulatory sequence.

38. A method of producing a polypeptide comprising:

(a) culturing the host cell of claim 37 under conditions such that said polypeptide is expressed; and (b) recovering said polypeptide.

39. The isolated polynucleotide of claim 8, further comprising a heterologous polynucleotide.

40. The isolated polynucleotide of 39, wherein the heterologous polynucleotide encodes a heterologous polypeptide.

41. A vector comprising the polynucleotide of claim 8.

42. An isolated host cell comprising the polynucleotide of claim 8, wherein said polynucleotide is operatively associated with a heterologous regulatory sequence.

* * * * *